United States Patent
Onda et al.

(10) Patent No.: US 9,409,158 B2
(45) Date of Patent: Aug. 9, 2016

(54) SYNTHESIS CATALYST AND SYNTHESIS METHOD FOR UNSATURATED CARBOXYLIC ACID AND/OR DERIVATIVE THEREOF

(71) Applicants: KABUSHIKI KAISHA SANGI, Tokyo (JP); KOCHI UNIVERSITY, Kochi (JP)

(72) Inventors: Ayumu Onda, Kochi (JP); Yumiko Matsuura, Kochi (JP); Kazumichi Yanagisawa, Kochi (JP); Jun Kubo, Tokyo (JP)

(73) Assignees: KABUSHIKI KAISHA SANGI, Tokyo (JP); KOCHI UNIVERSITY, Kochi (JP)

( * ) Notice: Subject to any disclaimer, the term of this patent is extended or adjusted under 35 U.S.C. 154(b) by 0 days.

(21) Appl. No.: 14/889,277

(22) PCT Filed: May 8, 2014

(86) PCT No.: PCT/JP2014/002448
§ 371 (c)(1),
(2) Date: Nov. 5, 2015

(87) PCT Pub. No.: WO2014/181545
PCT Pub. Date: Nov. 13, 2014

(65) Prior Publication Data
US 2016/0096166 A1    Apr. 7, 2016

(30) Foreign Application Priority Data

May 10, 2013   (JP) .................................. 2013-100404

(51) Int. Cl.
| | | |
|---|---|---|
| *B01J 27/14* | (2006.01) | |
| *C07C 51/347* | (2006.01) | |
| *B01J 35/00* | (2006.01) | |
| *B01J 27/18* | (2006.01) | |
| *C07C 67/327* | (2006.01) | |
| *B01J 37/10* | (2006.01) | |

(52) U.S. Cl.
CPC .............. *B01J 27/18* (2013.01); *B01J 27/1806* (2013.01); *B01J 37/10* (2013.01); *C07C 51/347* (2013.01); *C07C 67/327* (2013.01); *B01J 35/002* (2013.01)

(58) Field of Classification Search
CPC ............................ B01J 27/1806; C07C 51/377
See application file for complete search history.

(56) References Cited

U.S. PATENT DOCUMENTS

| | | | | |
|---|---|---|---|---|
| 4,729,978 A | * | 3/1988 | Sawicki | B01J 27/1806 502/174 |
| 4,792,620 A | * | 12/1988 | Paulik | B01J 31/0231 560/232 |
| 2014/0155653 A1 | * | 6/2014 | Dongare | C07C 51/377 562/599 |

FOREIGN PATENT DOCUMENTS

| | | |
|---|---|---|
| JP | 2000-169417 | 6/2000 |
| JP | 2006-015330 | 1/2006 |
| JP | 2009-067775 | 4/2009 |
| JP | 2012-071267 | 4/2012 |
| WO | 2011/052178 | 5/2011 |
| WO | 2012/063044 | 5/2012 |

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Ghantani et al., "Catalytic Dehydration of Lactic Acid to Acrylic Acid Using Calcium Hydroxyapatite Catalysts," Green Chemistry, Feb. 27, 2013, vol. 15, No. 5, pp. 1211-1217.
Matsumura et al., "Dehydration of Lactic Acid to Acrylic Acid Using Hydroxyapatite Catalyst," Journal of Dai 106 Kai Shokubai Toronakai, Sep. 9, 2010, p. 159. (Partial Translation Included).
Onda et al., Synthesis of Apatite Compound Microparticles Substituted by Various Elements and Application to Catalyst, Journal of the Society of Inorganic Materials, May 1, 2013. vol. 20, No. 364, pp. 172-182. (Partial Translation Included).

* cited by examiner

*Primary Examiner* — Paul A Zucker
(74) *Attorney, Agent, or Firm* — Occhiuti & Rohlicek LLP

(57) ABSTRACT

Using conventional synthesis methods, when an unsaturated carboxylic acid or a derivative thereof is synthesized from a hydroxycarboxylic acid or a derivative thereof by a dehydration reaction using a catalyst, the yield has been low. Accordingly, an object of the present invention is to provide a catalyst capable of synthesizing unsaturated carboxylic acids or derivatives thereof by a dehydration reaction that produces a high yield. The synthetic catalyst comprises an apatite compound containing an alkali metal in a crystal structure thereof, and the invention further includes methods for synthesizing an unsaturated carboxylic acid and/or a derivative thereof. The methods comprise contacting the aforementioned synthetic catalyst with the hydroxycarboxylic acid and/or a derivative thereof, so as to synthesize the unsaturated carboxylic acid and/or a derivative thereof by a dehydration reaction.

18 Claims, 4 Drawing Sheets

SYNTHESIS CATALYST AND SYNTHESIS METHOD FOR UNSATURATED CARBOXYLIC ACID AND/OR DERIVATIVE THEREOF

CROSS REFERENCE TO RELATED APPLICATIONS

This application is a National Stage of International Application No. PCT/JP2014/002448 filed on May 8, 2014, which claims priority to Japanese Application No. 2013-100404 filed on May 10, 2013, the contents of which are hereby incorporated by reference in their entirety.

TECHNICAL FIELD

The present invention relates to a method for synthesizing an unsaturated carboxylic acid and/or a derivative thereof from a hydroxycarboxylic acid and/or a derivative thereof, and a catalyst used therefor.

BACKGROUND ART

Acrylic acid is a raw material monomer for polyacrylic acid or acrylic acid copolymers. Because of an increase in the amount of a water-absorption resin (sodium polyacrylate) used, the amount of acrylic acid produced has been increased. Acrylic acid is generally produced by synthesizing acrolein from propylene that is a raw material derived from petroleum and then by converting this acrolein to acrylic acid by catalytic gas-phase oxidation (Patent Document 1). However, there is a fear that such a petroleum-derived raw material will be depleted in the future. Because of such a fear, studies have been conducted for the purpose of obtaining an unsaturated carboxylic acid from biomass, and for instance, a method for synthesizing an unsaturated carboxylic acid or an ester thereof from an ammonium salt of hydroxycarboxylic acid has been disclosed (Patent Document 2). However, the method described in the Patent Document 2 comprises complicated steps, such as the necessity of separating the ammonium salt of hydroxycarboxylic acid into a hydroxycarboxylic acid and a non-aqueous ammonium cation-containing exchange resin.

Hence, a method for synthesizing an unsaturated carboxylic acid or a derivative thereof from a biomass-derived hydroxycarboxylic acid or a derivative thereof by a dehydration reaction using hydroxyapatite ($Ca_{10}(PO_4)_6(OH)_2$) or $Sr_{10}(PO_4)_6(OH)_2$ as a catalyst has been proposed (Patent Document 3). Nevertheless, when acrylic acid is synthesized from lactic acid using the aforementioned hydroxyapatite, the yield of the acrylic acid is only approximately 50% to 70%, and when $Sr_{10}(PO_4)_6(OH)_2$, in which Ca in hydroxyapatite is replaced with Sr, is used as a catalyst, the yield of the acrylic acid is reduced to approximately 30%. Thus, it has been desired to develop a method for synthesizing an unsaturated carboxylic acid such as acrylic acid, or an ester thereof, at a higher yield.

PRIOR ART DOCUMENTS

Patent Documents

Patent Document 1: Japanese unexamined Patent Application Publication No. 2006-15330
Patent Document 2: Japanese unexamined Patent Application Publication No. 2009-67775
Patent Document 3: International Publication No. WO 2011/052178

SUMMARY OF INVENTION

Object to be Solved by the Invention

It is an object of the present invention to provide a catalyst, which solves a problem in that when an unsaturated carboxylic acid or a derivative thereof has been conventionally synthesized from a hydroxycarboxylic acid or a derivative thereof by a dehydration reaction using a catalyst, the yield has been low, and which is capable of synthesizing the unsaturated carboxylic acid or a derivative thereof at a high yield, and also to provide a synthetic method capable of synthesizing the unsaturated carboxylic acid or a derivative thereof at a high yield.

Means to Solve the Object

Upon the synthesis of an unsaturated carboxylic acid or a derivative thereof from a hydroxycarboxylic acid or a derivative thereof, the present inventors have focused on an apatite compound to be used as a catalyst, and have started studies regarding the improvement of the yield of the unsaturated carboxylic acid or a derivative thereof. However, although the inventors have altered the molar ratio Ca/P in hydroxyapatite and have examined the catalytic activity, effects higher than the conventional results could not be obtained. Thus, the present inventors have conducted further studies, and as a result, they have found that the yield of the unsaturated carboxylic acid or a derivative thereof is improved by allowing the apatite compound to contain an alkali metal. Moreover, the inventors have also found that when the content percentage of the alkali metal is in a specific range, the yield of the synthesized unsaturated carboxylic acid or a derivative thereof is significantly increased. The present invention has been completed based on the aforementioned findings.

Specifically, the present invention relates to: (1) a synthetic catalyst for synthesizing an unsaturated carboxylic acid and/or a derivative thereof from a hydroxycarboxylic acid and/or a derivative thereof by a dehydration reaction, wherein the synthetic catalyst comprises an apatite compound containing an alkali metal in a crystal structure thereof; (2) the synthetic catalyst according to (1) above, wherein the alkali metal is sodium and/or potassium; (3) the synthetic catalyst according to (1) or (2) above, wherein the content percentage of the alkali metal in the apatite compound is 0.2 to 3.0% by mass; (4) the synthetic catalyst according to any one of (1) to (3) above, wherein the apatite compound comprises calcium, phosphorus and an alkali metal, and (calcium+alkali metal)/phosphorus is 1.58 to 1.73 at a molar ratio; (5) the synthetic catalyst according to any one of (2) to (4) above, wherein when the alkali metal is sodium, the content percentage of the sodium in the apatite compound is 0.5 to 3.0% by mass, and when the alkali metal is potassium, the content percentage of the potassium in the apatite compound is 0.2 to 2.5% by mass; and (6) the synthetic catalyst according to any one of (2) to (5) above, wherein when the alkali metal is sodium, the content percentage of the sodium comprised in the crystal structure of the apatite compound is 0.5 to 1.6% by mass, and when the alkali metal is potassium, the content percentage of the potassium comprised in the crystal structure of the apatite compound is 0.2 to 1.5% by mass.

Moreover, the present invention relates to: (7) a method for synthesizing an unsaturated carboxylic acid and/or a derivative thereof, which method comprises contacting a hydroxycarboxylic acid and/or a derivative thereof with a catalyst to synthesize the unsaturated carboxylic acid and/or a derivative thereof by a dehydration reaction, wherein the catalyst is the synthetic catalyst according to any one of (1) to (6) above; and (8) the method for synthesizing an unsaturated carboxylic acid and/or a derivative thereof according to (7) above, which method comprises contacting the hydroxycarboxylic acid and/or a derivative thereof with the catalyst at a temperature of 325° C. to 400° C.

Effect of the Invention

According to the present invention, a catalyst capable of synthesizing an unsaturated carboxylic acid and/or a derivative thereof from a hydroxycarboxylic acid and/or a derivative thereof at a high yield can be provided. Moreover, a catalyst, which is less likely to be influenced by the concentration of the hydroxycarboxylic acid and/or a derivative thereof to be added to the synthetic reaction and which is capable of maintaining a high yield without depending on the aforementioned concentration, can be provided, and further, a catalyst, which is less likely to be influenced by a temperature in a predetermined temperature range and with which a synthetic reaction is carried out at a stable yield, can be provided. Furthermore, a method for synthesizing an unsaturated carboxylic acid and/or a derivative thereof at a high yield, in which the aforementioned catalyst is used, can be provided, and further, a synthetic method which is less likely to be influenced by the concentration of a raw material, or a synthetic method which is less likely to be influenced by a temperature in a predetermined temperature range, can be provided.

MODE OF CARRYING OUT THE INVENTION

Figure 1:
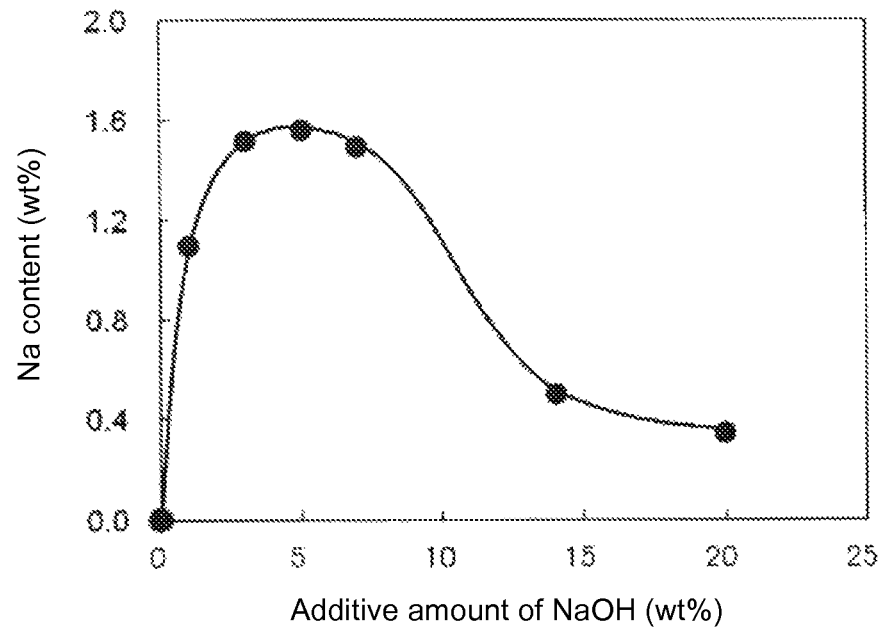
FIG. 1 is a view showing the relationship between the additive amount of NaOH and the content (content percentage) of Na in the synthesized apatite compound upon preparation of Samples 1 and 5 to 10.

The synthetic catalyst of the present invention used for synthesizing an unsaturated carboxylic acid and/or a derivative thereof is characterized in that it comprises an apatite compound containing an alkali metal in a crystal structure thereof. In general, the apatite compound is a compound having an apatite structure. The concept of the apatite compound includes a solid solution, and the compound represented by a general formula: $M_a(M'O_b)_cX_2$. A basic apatite compound is represented by $M_{10}(M'O_4)_6X_2$, wherein a is 10, b is 4, c is 6, and a/c is 1.67. However, the apatite compound of the present invention containing an alkali metal in a crystal structure thereof (hereinafter referred to as an "apatite composition") is not limited to the above described basic apatite compound, and a case in which a, b and c do not have the above described values is also included in the present apatite composition. When the apatite compound is a solid solution, when a/c is deviated from 1.67, when elements other than divalent elements are included in M, when elements other than pentavalent elements, such as C or S, are included in M', and the like, a, b and c have values different from the above described values. In the case of the apatite composition of the present invention, a/c is preferably between 1.5 and 1.8. In addition, in the case of the apatite composition of the present invention, M in the above-mentioned general formula is not particularly limited, and M can be, for example, one or more selected from Ca, Sr, Pb, Mg, Cd, Fe, Co, Ni, Cu, Zn, La, and H. Among these elements, Ca is preferable. Moreover, M' is not particularly limited, and M' can be, for example, one or more selected from P, V, As, C, and S. Among these elements, P or a combination of P with another element is preferable. X is not particularly limited, and examples of the X include OH, F, and Cl. The apatite composition of the present invention further contains an alkali metal in a crystal structure thereof. Examples of such an alkali metal include one or more selected from lithium (Li), sodium (Na), potassium (K), rubidium (Rb), cesium (Cs), and francium (Fr). Among these elements, sodium, potassium, or a combination of sodium with potassium is preferable.

The content of an alkali metal in the apatite composition of the present invention is not particularly limited. From the viewpoint of further enhancement of the yield of an unsaturated carboxylic acid or a derivative thereof, the content percentage of the alkali metal in the apatite composition is preferably 0.2 to 3.0% by mass. When sodium is used as such an alkali metal, the content percentage of the sodium is more preferably 0.5% to 3.0 by mass, even more preferably 0.5 to 1.6% by mass, and further preferably 0.7 to 1.6% by mass. When potassium is used as such an alkali metal, the content percentage of the potassium is more preferably 0.2 to 2.5% by mass, even more preferably 0.2 to 1.5% by mass, and further preferably 0.3 to 1.5% by mass. Moreover, when potassium is used, even if the content percentage of the potassium is low (0.4 to 0.7% by mass), the unsaturated carboxylic acid or a derivative thereof can be obtained at a high yield. Although the apatite composition of the present invention contains an alkali metal in a crystal structure thereof, it can also contain such an alkali metal outside of the crystal structure. Herein, the content percentage (% by mass) of an alkali metal means the ratio of the mass of the alkali metal to the total mass of an apatite compound (apatite composition) containing the alkali metal in a crystal structure thereof. The above-mentioned mass of the alkali metal means a total of the mass of an alkali metal contained in a crystal structure and the mass of an alkali metal contained in the outside of the crystal structure as a result of adhesion or deposition of the alkali metal on the surface of the apatite compound. Furthermore, the alkali metal is contained in the crystal structure of the apatite compound preferably in the above described content percentage range. When the alkali metal is sodium, the content percentage of the sodium contained in the crystal structure is preferably 0.5 to 1.6% by mass, and more preferably 0.7 to 1.6% by mass. When the alkali metal is potassium, the content percentage of the potassium contained in the crystal structure is preferably 0.2 to 1.5% by mass, more preferably 0.3 to 1.5% by mass, and even more preferably 0.4 to 0.7% by mass. Herein, the content percentage of the alkali metal contained in the crystal structure means the ratio of the mass of the alkali metal contained in the crystal structure to the total mass of an apatite composition.

In the apatite composition of the present invention, the relationship among the alkali metal and the M and M' in the aforementioned general formula ((M+alkali metal)/M') is preferably 1.58 to 1.73 at a molar ratio. If the molar ratio is in the above described range, the yield of the unsaturated carboxylic acid or a derivative thereof can be further enhanced. In addition, M is preferably calcium (Ca), and M' is preferably phosphorus (P). When the alkali metal is sodium (Na), (Ca+Na)/P is preferably 1.58 to 1.73, and more preferably 1.61 to 1.67 at a molar ratio. When the alkali metal is potassium (K), (Ca+K)/P is preferably 1.60 to 1.71, and more preferably 1.64 to 1.71 at a molar ratio. The number of moles of the alkali metal in the above described molar ratio means a total number of moles of the number of moles of the alkali metal contained in the crystal structure and the number of moles of the alkali metal contained in the outside of the crystal structure as a result of adhesion or deposition of the alkali metal on the surface of the apatite compound. Moreover, the relationship among the alkali metal contained in the crystal structure of the apatite compound and the M and M' in the aforementioned general formula ((M+the alkali metal contained in the crystal structure)/M') is preferably 1.58 to 1.73 at a molar ratio. When the alkali metal contained in the crystal structure is sodium, the above described molar ratio is preferably 1.58 to 1.73, and more preferably 1.61 to 1.67. When the alkali metal contained in the crystal structure is potassium, the molar ratio is preferably 1.60 to 1.71, and more preferably 1.64 to 1.71.

In the apatite composition of the present invention, an alkali metal is contained in the crystal structure of the apatite compound. The apatite compound, in the crystal structure of which the alkali metal is contained, has a higher effect as a catalyst than a case in which the alkali metal adheres to or deposited on the surface of the apatite compound, and thus, it is able to further enhance the yield of the unsaturated carboxylic acid or a derivative thereof. Moreover, if the alkali metal is contained in the crystal structure of the apatite compound, the apatite compound is also excellent in terms of stability as a catalyst. The catalyst of the present invention is a synthetic catalyst used for synthesizing an unsaturated carboxylic acid and/or a derivative thereof, which is characterized in that it comprises the apatite composition of the present invention. The synthetic catalyst of the present invention can only consist of the apatite composition of the present invention, or can also comprise other components. When the present synthetic catalyst comprises other components, it is preferable to apply substances and additive amounts that do not inhibit the catalytic function of the above described apatite composition.

The hydroxycarboxylic acid and/or a derivative thereof used as a raw material compound in the present invention are not particularly limited. Examples of the hydroxycarboxylic acid and/or a derivative thereof include hydroxycarboxylic acids such as lactic acid, citric acid, 3-hydroxypropionic acid, 3-hydroxy-2-methylpropionic acid, 3-hydroxybutanoic acid, 3-hydroxy-2-methylbutanoic acid and 2,3-dimethyl-3-hydroxybutanoic acid, and the derivatives thereof, such as their salts or esters. In addition, biomass-derived hydroxycarboxylic acids can also be used. The unsaturated carboxylic acid and/or a derivative thereof synthesized in the present invention are not particularly limited, and examples include unsaturated carboxylic acids such as acrylic acid and methacrylic acid, and the derivatives thereof such as their esters.

The apatite composition of the present invention can be synthesized, for example, by a hydrothermal reaction. The hydrothermal reaction can be carried out, for example, by mixing the aqueous solutions of individual raw material compounds including alkali metal sources such as phosphoric acid, calcium nitrate and sodium hydroxide, adjusting the pH of the obtained mixture, and then reacting it at a temperature of approximately 50° C. to 300° C. under a pressure of approximately $1\times10^5$ to $1\times10^7$ Pa. By adjusting the ratio of the amounts of individual raw material compounds used and the pH, the content percentage of the alkali metal can be changed. For example, in the case of a calcium- or phosphorus-based apatite compound, since calcium (Ca)/phosphorus (P) is 1.67 at a molar ratio in an apatite compound having a basic structure, raw materials are mixed with one another, such that the molar ratio Ca/P can be smaller than 1.67, and an apatite compound is then synthesized in a state in which Ca is insufficient, so that the alkali metal can be incorporated into the crystal structure of the apatite compound.

The method of the present invention for synthesizing an unsaturated carboxylic acid and/or a derivative thereof is a method for synthesizing an unsaturated carboxylic acid and/or a derivative thereof, which method comprises contacting a hydroxycarboxylic acid and/or a derivative thereof used as a raw material compound with the synthetic catalyst of the present invention, so as to synthesize the unsaturated carboxylic acid and/or a derivative thereof by a dehydration reaction. The synthetic method of the present invention is preferably carried out by vaporizing an aqueous solution of a hydroxycarboxylic acid or a derivative thereof and then contacting it with the synthetic catalyst of the present invention. This is because condensation of the hydroxycarboxylic acid or a derivative thereof before it is introduced into a reaction tube can be suppressed, and also because if the reaction product is cooled in an ice bath trap or the like, it is converted to an aqueous solution containing an unsaturated carboxylic acid or a derivative thereof, and thus it is easily recovered. However, even if there is no solvent, the reaction progresses. In order to further enhance the yield of the unsaturated carboxylic acid or a derivative thereof to be synthesized, the reaction temperature is preferably 325° C. to 400° C., and more preferably 325° C. to 375° C. The reaction pressure can be any condition of an ordinary pressure, an increased pressure, and a reduced pressure. The concentration of an aqueous solution of a hydroxycarboxylic acid or a derivative thereof is not particularly limited. Taking into consideration efficiency, the concentration of the aqueous solution of the hydroxycarboxylic acid or a derivative thereof is preferably 20 to 50% by mass. The solution of the hydroxycarboxylic acid or a derivative thereof can contain a solvent other than water. In the case of hydroxycarboxylic acid, a hydrophilic organic solvent such as alcohol or ether can be used together with water, or instead of water. Moreover, when a hydroxycarboxylic acid ester that is a derivative of hydroxycarboxylic acid is unlikely to be dissolved or is not dissolved in water, the reaction can be carried out without using solvents, or an organic solvent that can solubilize the hydroxycarboxylic acid ester can be used.

The reaction type for carrying out the synthetic reaction is not particularly limited, and examples of the reaction type include such as a fixed bed type, a moving bed type, and a fluidized bed type. Further, as a carrier gas, an inert gas such as nitrogen, argon or helium can be used. In the case of using a fixed bed fluidized-type reactor, for example, inert filler such as silica wool or quartz sand can be used to the upstream or downstream of a catalytic layer. The reaction product is purified by known purification means such as distillation or crystallization, so that a high-purity unsaturated carboxylic acid or a derivative thereof can be obtained.

EXAMPLES

Hereinafter, the present invention will be more specifically described in the following examples. However, the technical scope of the present invention is not limited to these examples.
(Preparation of Catalysts)
(Preparation of Comparative Catalysts)
[Sample 1]

Solution A prepared by adding 7 mmol of $NH_3$ water to 2.35 mmol of $H_3PO_4$ aqueous solution was mixed with Solution B prepared by dissolving 3.53 mmol of $Ca(NO_3)_2 \cdot 4H_2O$ in distilled water, and the mixed solution was then subjected to a hydrothermal treatment at 110° C. for 14 hours. Thereafter, the obtained white solid was centrifuged, was then washed with water, and was then dried at 60° C. The obtained powders were molded into powders having a particle diameter of 250 to 500 μm, and were then used in a catalytic reaction test.
[Sample 2]

Solution A prepared by adding 7 mmol of $NH_3$ water to 2.35 mmol of $H_3PO_4$ aqueous solution was mixed with Solution B prepared by dissolving 4.40 mmol of $Ca(NO_3)_2 \cdot 4H_2O$ in distilled water, and the mixed solution was then subjected to a hydrothermal treatment at 110° C. for 14 hours. Thereafter, the obtained white solid was centrifuged, was then washed with water, and was then dried at 60° C. The obtained powders were molded into powders having a particle diameter of 250 to 500 μm, and were then used in a catalytic reaction test.
[Sample 3]

1 g of Sample 2 was impregnated with 0.6 mmol of NaOH, and it was then dried at 60° C. The obtained powders were molded into powders having a particle diameter of 250 to 500 μm, and were then used in a catalytic reaction test.
[Sample 4]

1 g of Sample 2 was impregnated with 0.6 mmol of KOH, and it was then dried at 60° C. The obtained powders were molded into powders having a particle diameter of 250 to 500 μm, and were then used in a catalytic reaction test.
(Preparation of the Catalysts of the Present Invention)
[Samples 5 to 10]

Solution A prepared by adding each of 1, 3, 5, 7, 14 and 20 mmol of NaOH to 2.35 mmol of $H_3PO_4$ aqueous solution was mixed with Solution B prepared by dissolving 3.53 mmol of $Ca(NO_3)_2 \cdot 4H_2O$ in distilled water, and the mixed solution was then subjected to a hydrothermal treatment at 110° C. for 14 hours. Thereafter, the obtained white solid was centrifuged, was then washed with water, and was then dried at 60° C. The obtained powders were molded into powders having a particle diameter of 250 to 500 μm, and were then used in a catalytic reaction test.
[Samples 11 and 12]

Solution A prepared by adding 7 mmol of NaOH to 2.35 mmol of $H_3PO_4$ aqueous solution was mixed with Solution B prepared by dissolving each of 3.65 and 3.77 mmol of $Ca(NO_3)_2 \cdot 4H_2O$ in distilled water, and the mixed solution was then subjected to a hydrothermal treatment at 110° C. for 14 hours. Thereafter, the obtained white solid was centrifuged, was then washed with water, and was then dried at 60° C. The obtained powders were molded into powders having a particle diameter of 250 to 500 μm, and were then used in a catalytic reaction test.

[Samples 13 and 14]

White solids, which had been obtained by mixing the same raw materials at the same mixing ratios as those of Samples 8 and 11 and then subjecting the mixed solutions to a hydrothermal treatment under the same conditions as those for Samples 8 and 11, were centrifuged, and were then dried at 60° C., without being subjected to water washing. The obtained samples were defined as Samples 13 and 14, respectively. The obtained powders were molded into powders having a particle diameter of 250 to 500 μm, and were then used in a catalytic reaction test.
[Samples 15 to 17]

Solution A prepared by adding 8 mmol of KOH to 2.53 mmol of $H_3PO_4$ aqueous solution was mixed with Solution B prepared by dissolving 3.53 mmol of $Ca(NO_3)_2 \cdot 4H_2O$ in distilled water, and the mixed solution was then subjected to a hydrothermal treatment at 110° C. for 14 hours. Thereafter, the obtained white solid was centrifuged, was then washed with water, and was then dried at 60° C. The obtained powders were molded into powders having a particle diameter of 250 to 500 μm, and were then used in a catalytic reaction test.
[Samples 18 and 19]

White solids, which had been obtained by mixing the same raw materials at the same mixing ratios as those of Samples 15 and 16 and then subjecting the mixed solutions to a hydrothermal treatment under the same conditions as those for Samples 15 and 16, were centrifuged, and were then dried at 60° C., without being subjected to water washing. The obtained samples were defined as Samples 18 and 19, respectively. The obtained powders were molded into powders having a particle diameter of 250 to 500 μm, and were then used in a catalytic reaction test.

Example 1

The apatite compounds in the thus prepared Samples 3 and 5 to 14 contained Na. The apatite compounds in the aforementioned Samples 1 to 3 were defined as comparative examples. Using Samples 1 to 3 and 5 to 14, a reaction of synthesizing acrylic acid from lactic acid was carried out. An ordinary pressure fixed bed fluidized-type reactor was used in the reaction, and as a pretreatment of a catalyst, calcination was performed under an Ar current at 500° C. for 3 hours. Lactic acid having a concentration of 38% by mass that was used as a reaction raw material was introduced into the preheated Ar current, so that it was allowed to come into contact with the catalyst. The amount of the catalyst was set at 1.0 g, and the reaction was carried out at a reaction temperature of 350° C. for 6 hours. Among gases passing through the catalytic layer, a liquid product captured in an ice bath and a gaseous product discharged from the outlet of an ice bath trap were recovered separately. The liquid product was analyzed by mass measurement using an electronic balance, high performance liquid chromatography (HPLC), GC-MS, GC-FID, GC-TCD, and a total organic carbon meter. The gaseous product was analyzed using GC-FID and GC-TCD. The reaction results are summarized in Table 1. Based on the area ratios of lactic acid and acrylic acid standard solutions in the HPLC chart, the lactic acid conversion was obtained by the formula {1−(area value of lactic acid of product/area value of standard sample)}×100, and the yield of the synthesized acrylic acid was obtained by the formula (area value of acrylic acid/area value of standard sample)×100. It is to be noted that the standard sample of lactic acid was defined as a solution obtained by adding 30 ml of 0.46 M NaOH aqueous solution to 0.5 g of 38% by mass of lactic acid aqueous solution, and that the standard sample of acrylic acid was defined as a solution obtained by adding 30 ml of 0.46 M NaOH aqueous solution to 30.4% by mass of acrylic acid aqueous solution.

TABLE 1

| | Composition of raw materials | In apatite compound | | | | | | |
|---|---|---|---|---|---|---|---|---|
| | Additive amount of alkali metal source (mmol) | Ca/P | Ca/P | (Ca + Na)/P | Na (mmol/g) | Na content percentage (wt %) | Lactic acid conversion (%) | Yield of acrylic acid (%) |
| Sample 1 | 0 | 1.50 | 1.50 | 1.50 | 0.00 | 0.00 | 99 | 69 |
| Sample 2 | 0 | 1.87 | 1.67 | 1.67 | 0.00 | 0.00 | 92 | 53 |
| Sample 3 | 0.6 | 1.67 | 1.67 | 1.76 | 0.52 | 1.20 | 84 | 32 |
| Sample 5 | 1 | 1.50 | 1.50 | 1.58 | 0.10 | 1.10 | 99 | 76 |
| Sample 6 | 3 | 1.50 | 1.51 | 1.61 | 0.66 | 1.52 | 96 | 81 |
| Sample 7 | 5 | 1.50 | 1.53 | 1.63 | 0.68 | 1.56 | 97 | 85 |
| Sample 8 | 7 | 1.50 | 1.56 | 1.66 | 0.65 | 1.50 | 97 | 86 |
| Sample 9 | 14 | 1.50 | 1.68 | 1.72 | 0.22 | 0.51 | 88 | 75 |
| Sample 10 | 20 | 1.50 | 1.73 | 1.75 | 0.15 | 0.35 | 80 | 61 |
| Sample 11 | 7 | 1.55 | 1.61 | 1.67 | 0.34 | 0.78 | 96 | 84 |
| Sample 12 | 7 | 1.60 | 1.67 | 1.73 | 0.21 | 0.48 | 91 | 77 |
| Sample 13 | 7 | 1.50 | 1.56 | 1.71 | 1.29 | 2.97 | 95 | 75 |
| Sample 14 | 7 | 1.55 | 1.60 | 1.82 | 1.68 | 3.86 | 89 | 68 |

(Lactic acid concentration: 38% by mass, reaction temperature: 350° C., catalytic amount: 1.0 g, Ar flow rate: 40 mL/min))

Figure 2:
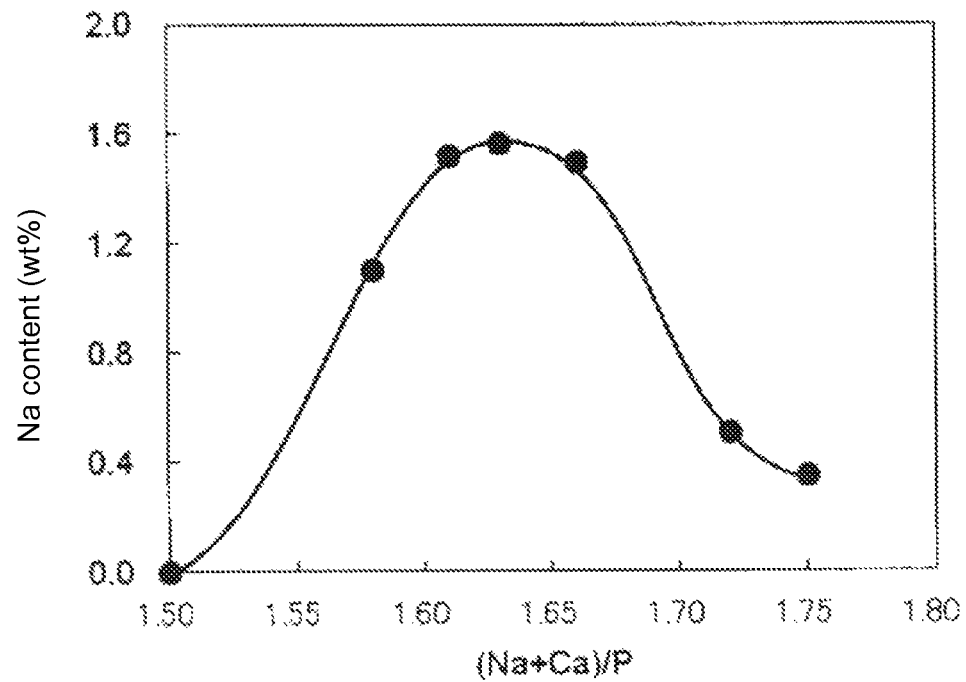
FIG. 2 is a view showing the relationship between the molar ratio (Ca+Na)/P and the content (content percentage) of Na in the synthesized apatite compound upon preparation of Samples 1 and 5 to 10.

As shown in Table 1, when the apatite compounds containing Na in Samples 5 to 14 were each allowed to come into contact with lactic acid, and thus they were reacted, acrylic acid was synthesized by a dehydration reaction. Samples 1 and 5 to 10 were prepared by altering the additive amount of NaOH used as an alkali metal source, while keeping the molar ratio Ca/P in the composition of the raw materials constant. When 5 mmol of NaOH was added (Sample 7), the content percentage of Na in the apatite compound became largest at 1.56% by mass, and when NaOH was added in an amount larger than the aforementioned amount, the content percentage of Na rather reduced. The relationship between the additive amount of NaOH and the content (content percentage) of Na upon preparation of Samples 1 and 5 to 10 is shown in FIG. 1. In addition, in the stoichiometric composition of hydroxyapatite, the molar ratio Ca/P was approximately 1.67. Upon preparation of Samples 1 and 5 to 10, the content percentage of Na in the apatite compound decreased, as the molar ratio (Ca+Na)/P came close to 1.67. The relationship between the molar ratio (Ca+Na)/P and the content (content percentage) of Na in Samples 1 and 5 to 10 is shown in FIG. 2. On the other hand, in the case of Samples 13 and 14, which had been prepared under the same conditions as those for Samples 8 and 11 and had not been subjected to water washing, the content percentage of Na increased in comparison to Samples 8 and 11. From these results, it is found that Na was contained in the crystal structure of the apatite compound in Samples 5 to 12, whereas in Samples 13 and 14, Na was contained in the crystal structure of the apatite compound, and was also contained in a state in which it was adhered to or was deposited on the surface of the compound. Moreover, since Sample 3 was obtained by impregnating Sample 2 containing no Na with NaOH, Na was not contained in the crystal structure of the apatite compound, but was adhered to or was deposited on the surface of the compound. Thus, even if Sample 3 contained Na, the yield of acrylic acid was significantly decreased in comparison to Sample 1 or 2 that did not contain Na. Hence, it is found that when Na is not contained in the crystal structure of the apatite compound, but is deposited on the surface of the compound, the catalytic activity was rather poisoned with Na. It is to be noted that "% by mass" is indicated as "wt %" in the figures and tables.

Figure 3:
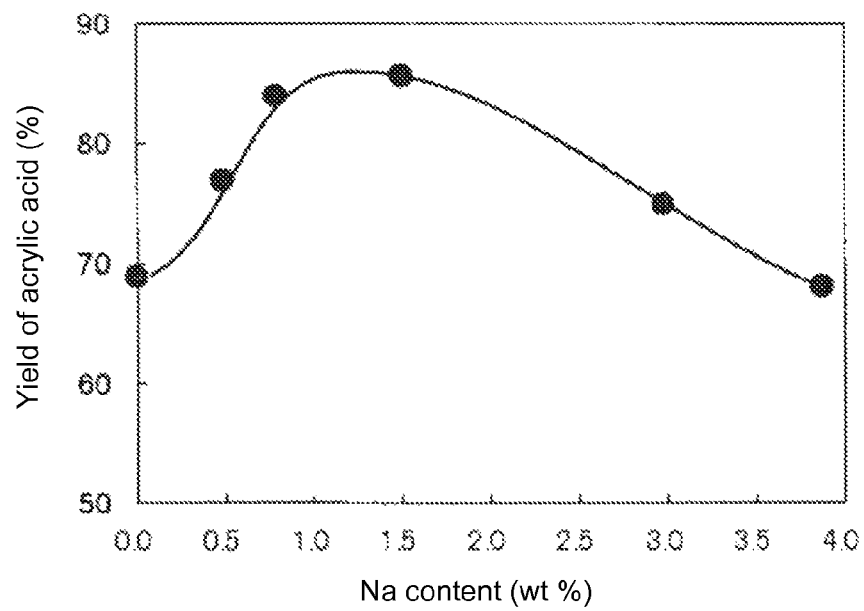
FIG. 3 is a view showing the relationship between the content (content percentage) of Na and the yield of acrylic acid in Example 1.
Figure 4:
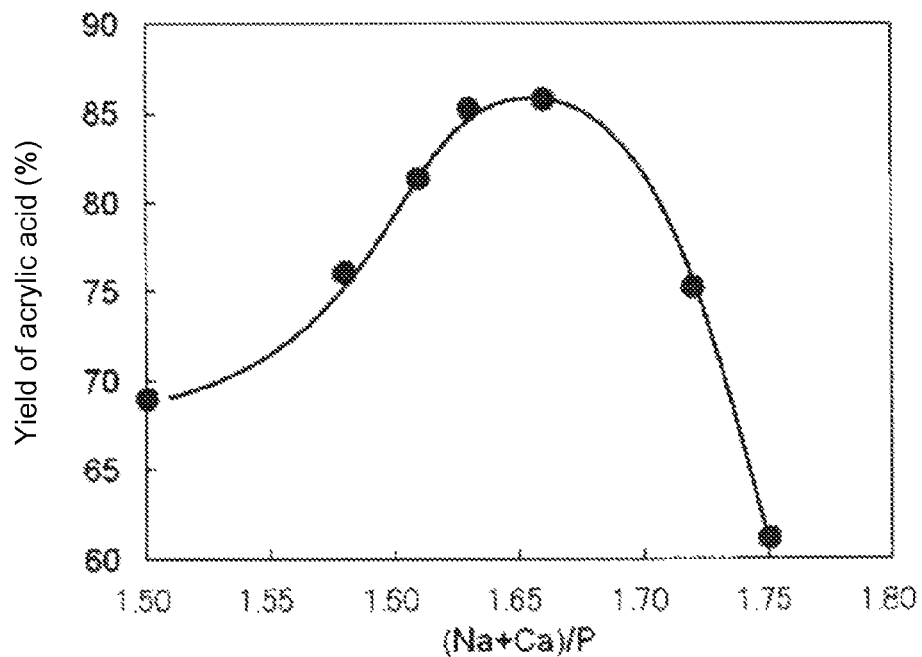
FIG. 4 is a view showing the relationship between the molar ratio (Ca+Na)/P and the yield of acrylic acid in Example 1.

Furthermore, when the content percentage of Na in the apatite compound was in the range of 0.5 to 3.0% by mass, acrylic acid could be obtained at a high yield such as 75% to 86%. If the content percentage of Na exceeded 3% by mass, the yield of acrylic acid became the same level as in the case of not containing Na. Hence, catalytic effects could be improved by allowing the apatite compound to contain Na in the crystal structure thereof. When the amount of Na that was not incorporated into the crystal structure increased, catalytic effects rather reduced. The relationship between the content (content percentage) of Na and the yield of acrylic acid in the results of Samples 1, 8, and 11 to 14 is shown in FIG. 3. Moreover, when the molar ratio (Ca+Na)/P was in the range of 1.58 to 1.73, acrylic acid could be obtained at a high yield such as 75% or more. The relationship between the molar ratio (Ca+Na)/P and the yield of acrylic acid in Samples 1 and 5 to 10 is shown in FIG. 4.

Example 2

Figure 5:
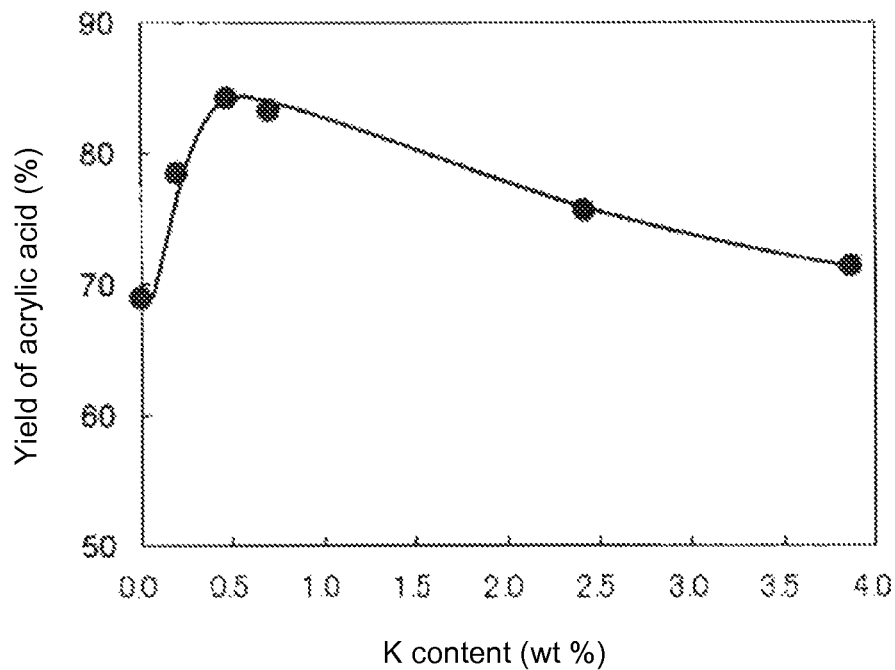
FIG. 5 is a view showing the relationship between the content (content percentage) of K and the yield of acrylic acid in Example 2.

The apatite compounds in the thus prepared Samples 4 and 15 to 19 contained K. The apatite compounds in the aforementioned Samples 1, 2 and 4 were defined as comparative examples. Using Samples 1, 2, 4 and 15 to 19, a reaction of synthesizing acrylic acid from lactic acid was carried out under the same reaction conditions as those in Example 1. The reaction results are summarized in Table 2. As shown in Table 2, when the apatite compounds containing K in Samples 15 to 19 were each allowed to come into contact with lactic acid, and thus they were reacted, acrylic acid was synthesized by a dehydration reaction. In the case of Samples 18 and 19, which had been prepared under the same conditions as those for Samples 15 and 16 and had not been subjected to water washing, the content percentage of K increased in comparison to Samples 15 and 16. In Samples 15 to 17, K was contained in the crystal structure of the apatite compound, and in Samples 18 and 19, K was contained in the crystal structure of the apatite compound and was also contained in a state in which it was adhered to or was deposited on the surface of the compound. In addition, when the content percentage of K in the apatite compound was in the range of 0.2 to 3.0% by mass, acrylic acid could be obtained at a high yield such as 76% to 84%. If the content percentage of K exceeded 3% by mass, the yield of acrylic acid came close to the case of not containing K. Hence, catalytic effects could be improved by allowing the apatite compound to contain K in the crystal structure thereof. When the amount of K that was not incorporated into the crystal structure increased, catalytic effects rather reduced. The relationship between the content (content percentage) of K and the yield of acrylic acid in the results of Samples 1 and 15 to 19 is shown in FIG. 5. Moreover, when the molar ratio (Ca+K)/P was in the range of 1.64 to 1.71, acrylic acid could be obtained at a high yield such as 72% or more. In case of using potassium, when the content percentage of potassium is 0.2-2.5% by mass, acrylic acid could be obtained at a high yield of 75% or more, and even when the content percentage of potassium is as low as 0.4-0.7% by mass, acrylic acid could be obtained at a high yield of 80% or more. Thus, acrylic acid could be obtained at a high yield, although the content percentage of K was lower than the content percentage of Na. Moreover, since Sample 4 was obtained by impregnating Sample 2 containing no K with KOH, K was not contained in the crystal structure of the apatite compound, but was adhered to or was deposited on the surface of the compound. Thus, even if Sample 4 contained K, the yield of acrylic acid was significantly reduced in comparison to Sample 1 or 2 that did not contain K. Hence, it is found that when K is not contained in the crystal structure of the apatite compound, but is deposited on the surface of the apatite compound, the catalytic activity was rather poisoned with K.

TABLE 2

| | Composition of raw materials | | In apatite compound | | | | | |
|---|---|---|---|---|---|---|---|---|
| | Additive amount of alkali metal source (mmol) | Ca/P | Ca/P | (Ca + K)/P | K (mmol/g) | K content percentage (wt %) | Lactic acid conversion (%) | Yield of acrylic acid (%) |
| Sample 1 | 0 | 1.50 | 1.50 | 1.50 | 0.00 | 0.00 | 99 | 69 |
| Sample 2 | 0 | 1.87 | 1.67 | 1.67 | 0.00 | 0.00 | 92 | 53 |
| Sample 4 | 0.6 | 1.67 | 1.67 | 1.76 | 0.58 | 2.26 | 78 | 28 |
| Sample 15 | 8 | 1.50 | 1.61 | 1.64 | 0.18 | 0.70 | 95 | 83 |
| Sample 16 | 8 | 1.55 | 1.63 | 1.65 | 0.12 | 0.47 | 94 | 84 |
| Sample 17 | 8 | 1.60 | 1.68 | 1.71 | 0.05 | 0.20 | 95 | 79 |
| Sample 18 | 8 | 1.50 | 1.60 | 1.68 | 0.62 | 2.42 | 95 | 76 |
| Sample 19 | 8 | 1.55 | 1.64 | 1.70 | 0.99 | 3.86 | 95 | 72 |

(Lactic acid concentration: 38% by mass, reaction temperature: 350° C., catalytic amount: 1.0 g, Ar flow rate: 40 mL/min)

Example 3

(Influence of Reaction Temperature)

Figure 6:
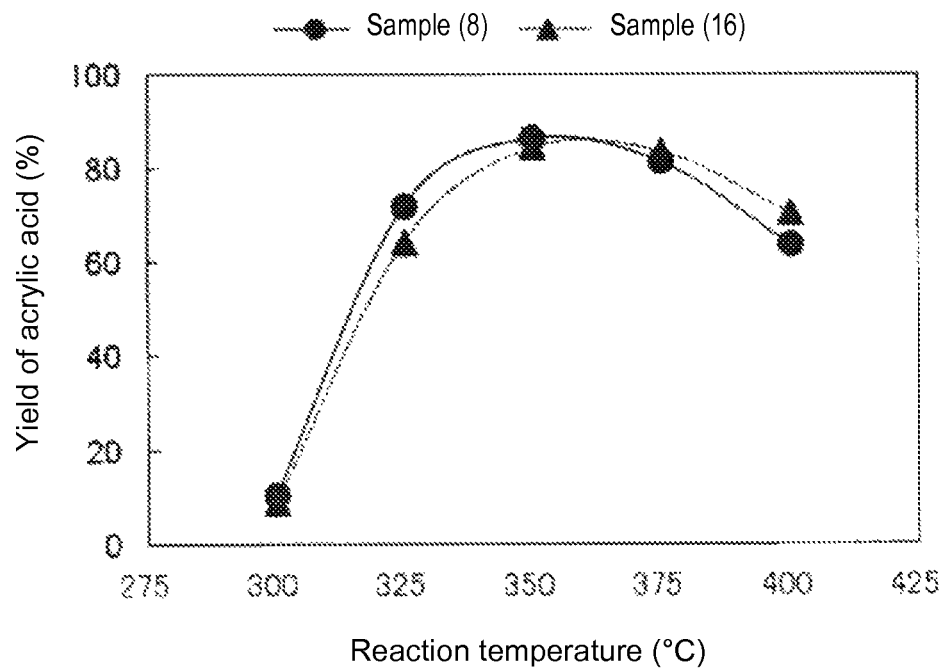
FIG. 6 is a view showing the relationship between the reaction temperature and the yield of acrylic acid in Example 3.

Sample 8 and Sample 16 were subjected to a synthetic reaction under the same reaction conditions as those in Example 1, with the exception that the reaction temperature was altered in the range of 300° C. to 400° C. The relationship between the reaction temperature and the yield of acrylic acid in the obtained results is shown in FIG. 6. When the reaction temperature was 300° C., a large amount of lactide was generated, and thus, the yield of acrylic acid was low. On the other hand, when the reaction temperature was 325° C. or higher, acrylic acid was obtained as a main product at a high yield. A reduction in the yield of acrylic acid at a reaction temperature of 400° C. was mainly caused by generation of a coke component. In a reaction temperature range of 325° C. to 400° C., and in particular, of 325° C. to 375° C., acrylic acid was stably obtained at a high yield, without being influenced by the temperature.

Example 4

(Influence of Lactic Acid Concentration)

Figure 7:
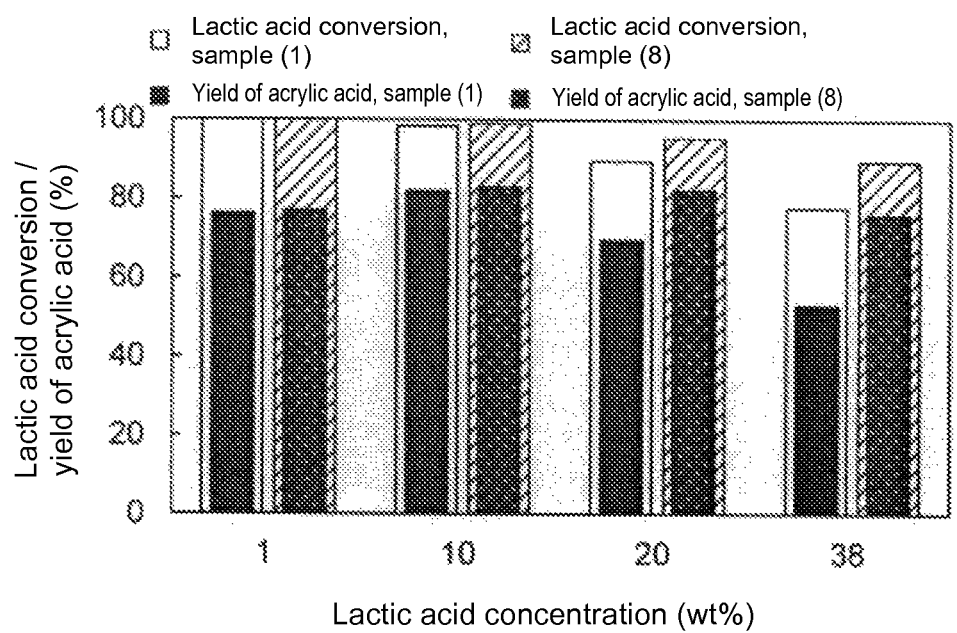
FIG. 7 is a view showing the relationship between the lactic acid concentration and the lactic acid conversion/the yield of acrylic acid in Example 4.

Sample 1 and Sample 8 were subjected to a synthetic reaction under the same reaction conditions as those in Example 1, with the exceptions that the concentration of a lactic acid aqueous solution was changed to 1, 10, 20, and 38% by mass, and that the amount of the catalyst was changed to 0.4 g. In the case of Sample 1 that did not contain sodium, the lactic acid conversion and the yield of acrylic acid significantly decreased, as the concentration of lactic acid increased. The yield of acrylic acid was 53% at a lactic acid concentration of 38% by mass. In contrast, in the case of Sample 8 that contained sodium, such reductions were small, and the yield of acrylic acid was maintained at a high standard (76%) at a lactic acid concentration of 38% by mass. The results are shown in FIG. 7.

Example 5

(Reaction of Ethyl Lactate)

Ethyl lactate was used as a raw material compound, instead of lactic acid, and a reaction of synthesizing ethyl acrylate was carried out using Samples 1 and 8. The reaction was carried out under the same reaction conditions as those in Example 1, with the exceptions that ethyl lactate was used instead of lactic acid, and that the concentration of the ethyl lactate was set at 100% by mass. The reaction product was analyzed in the same manner as that in Example 1, with the exception that it was 10 times diluted with methanol when it was analyzed by GC-MS and GC-FID. The conversion of ethyl lactate was 55% in the case of Sample 1, whereas it was 65% in the case of Sample 8. In addition, the yield of ethyl acrylate was 18% in the case of Sample 1, whereas it was 26% in the case of Sample 8.

INDUSTRIAL APPLICABILITY

According to the method of the present invention, an unsaturated carboxylic acid and/or a derivative thereof can be synthesized from a hydroxycarboxylic acid and/or a derivative thereof at a high yield, and for example, a hydroxycarboxylic acid and/or a derivative thereof derived from biomass can be used. Therefore, it becomes possible to synthesize an industrially useful unsaturated carboxylic acid and/or a derivative thereof without relying on petroleum feedstock.

The invention claimed is:

1. A synthetic catalyst for synthesizing an unsaturated carboxylic acid and/or a derivative thereof from a hydroxycarboxylic acid and/or a derivative thereof by a dehydration reaction, wherein the synthetic catalyst comprises an apatite compound containing an alkali metal in the crystal structure thereof, wherein the alkali metal is sodium and/or potassium, wherein the content percentage of the alkali metal in the apatite compound is 0.2 to 3.0% by mass, wherein the hydroxycarboxylic acid is lactic acid, citric acid, 3-hydroxypropionic acid, 3-hydroxy-2-methylpropionic acid, 3-hydroxybutanoic acid, 3-hydroxy-2-methylbutanoic acid or 2,3-dimethyl-3-hydroxybutanoic acid, wherein the derivative is a salt or ester, and wherein the unsaturated carboxylic acid and/or a derivative thereof is an unsaturated carboxylic acid and/or a salt or ester thereof.

2. The synthetic catalyst according to claim 1, wherein the apatite compound comprises calcium, phosphorus and an alkali metal, and (calcium+alkali metal)/phosphorus is 1.58 to 1.73 at a molar ratio.

3. The synthetic catalyst according to claim 1, wherein when the alkali metal is sodium, the content percentage of the sodium in the apatite compound is 0.5 to 3.0% by mass, and when the alkali metal is potassium, the content percentage of the potassium in the apatite compound is 0.2 to 2.5% by mass.

4. The synthetic catalyst according to claim 1, wherein when the alkali metal is sodium, the content percentage of the sodium comprised in the crystal structure of the apatite compound is 0.5 to 1.6% by mass, and when the alkali metal is potassium, the content percentage of the potassium comprised in the crystal structure of the apatite compound is 0.2 to 1.5% by mass.

5. A method for synthesizing an unsaturated carboxylic acid and/or a derivative thereof, which method comprises contacting a hydroxycarboxylic acid and/or a derivative thereof with a catalyst to synthesize the unsaturated carboxylic acid and/or a derivative thereof by a dehydration reaction, wherein the hydroxycarboxylic acid is lactic acid, citric acid, 3-hydroxypropionic acid, 3-hydroxy-2-methylpropionic acid, 3-hydroxybutanoic acid, 3-hydroxy-2-methylbutanoic acid or 2,3-dimethyl-3-hydroxybutanoic acid, wherein the derivative is a salt or ester, wherein the unsaturated carboxylic acid and/or a derivative thereof is an unsaturated carboxylic acid and/or a salt or ester thereof, and wherein the catalyst is the synthetic catalyst according to claim 1.

6. The method for synthesizing an unsaturated carboxylic acid and/or a derivative thereof according to claim 5, which method comprises contacting the hydroxycarboxylic acid and/or a derivative thereof with the catalyst at a temperature of 325° C. to 400° C.

7. The synthetic catalyst according to claim 3, wherein the apatite compound comprises calcium, phosphorus and an alkali metal, and (calcium+alkali metal)/phosphorus is 1.58 to 1.73 at a molar ratio.

8. The synthetic catalyst according to claim 4, wherein the apatite compound comprises calcium, phosphorus and an alkali metal, and (calcium+alkali metal)/phosphorus is 1.58 to 1.73 at a molar ratio.

9. A method for synthesizing an unsaturated carboxylic acid and/or a derivative thereof, which method comprises contacting a hydroxycarboxylic acid and/or a derivative thereof with a catalyst to synthesize the unsaturated carboxylic acid and/or a derivative thereof by a dehydration reaction, wherein the hydroxycarboxylic acid is lactic acid, citric acid, 3-hydroxypropionic acid, 3-hydroxy-2-methylpropionic acid, 3-hydroxybutanoic acid, 3-hydroxy-2-methylbutanoic acid or 2,3-dimethyl-3-hydroxybutanoic acid, wherein the derivative is a salt or ester, wherein the unsaturated carboxylic acid and/or a derivative thereof is an unsaturated carboxylic acid and/or a salt or ester thereof, and wherein the catalyst is the synthetic catalyst according to claim 2.

10. A method for synthesizing an unsaturated carboxylic acid and/or a derivative thereof, which method comprises contacting a hydroxycarboxylic acid and/or a derivative thereof with a catalyst to synthesize the unsaturated carboxylic acid and/or a derivative thereof by a dehydration reaction, wherein the hydroxycarboxylic acid is lactic acid, citric acid, 3-hydroxypropionic acid, 3-hydroxy-2-methylpropionic acid, 3-hydroxybutanoic acid, 3-hydroxy-2-methylbutanoic acid or 2,3-dimethyl-3-hydroxybutanoic acid, wherein the derivative is a salt or ester, wherein the unsaturated carboxylic acid and/or a derivative thereof is an unsaturated carboxylic acid and/or a salt or ester thereof, and wherein the catalyst is the synthetic catalyst according to claim 3.

11. A method for synthesizing an unsaturated carboxylic acid and/or a derivative thereof, which method comprises contacting a hydroxycarboxylic acid and/or a derivative thereof with a catalyst to synthesize the unsaturated carboxylic acid and/or a derivative thereof by a dehydration reaction, wherein the hydroxycarboxylic acid is lactic acid, citric acid, 3-hydroxypropionic acid, 3-hydroxy-2-methylpropionic acid, 3-hydroxybutanoic acid, 3-hydroxy-2-methylbutanoic acid or 2,3-dimethyl-3-hydroxybutanoic acid, wherein the derivative is a salt or ester, wherein the unsaturated carboxylic acid and/or a derivative thereof is an unsaturated carboxylic acid and/or a salt or ester thereof, and wherein the catalyst is the synthetic catalyst according to claim 4.

12. A method for synthesizing an unsaturated carboxylic acid and/or a derivative thereof, which method comprises contacting a hydroxycarboxylic acid and/or a derivative thereof with a catalyst to synthesize the unsaturated carboxylic acid and/or a derivative thereof by a dehydration reaction, wherein the hydroxycarboxylic acid is lactic acid, citric acid, 3-hydroxypropionic acid, 3-hydroxy-2-methylpropionic acid, 3-hydroxybutanoic acid, 3-hydroxy-2-methylbutanoic acid or 2,3-dimethyl-3-hydroxybutanoic acid, wherein the derivative is a salt or ester, wherein the unsaturated carboxylic acid and/or a derivative thereof is an unsaturated carboxylic acid and/or a salt or ester thereof, and wherein the catalyst is the synthetic catalyst according to claim 7.

13. A method for synthesizing an unsaturated carboxylic acid and/or a derivative thereof, which method comprises contacting a hydroxycarboxylic acid and/or a derivative thereof with a catalyst to synthesize the unsaturated carboxylic acid and/or a derivative thereof by a dehydration reaction, wherein the hydroxycarboxylic acid is lactic acid, citric acid, 3-hydroxypropionic acid, 3-hydroxy-2-methylpropionic acid, 3-hydroxybutanoic acid, 3-hydroxy-2-methylbutanoic acid or 2,3-dimethyl-3-hydroxybutanoic acid, wherein the derivative is a salt or ester, wherein the unsaturated carboxylic acid and/or a derivative thereof is an unsaturated carboxylic acid and/or a salt or ester thereof, and wherein the catalyst is the synthetic catalyst according to claim 8.

14. The method for synthesizing an unsaturated carboxylic acid and/or a derivative thereof according to claim 9, which method comprises contacting the hydroxycarboxylic acid and/or a derivative thereof with the catalyst at a temperature of 325° C. to 400° C.

15. The synthetic catalyst according to claim 1, wherein the hydroxycarboxylic acid and/or a derivative thereof is lactic acid and/or a salt or ester thereof, and wherein the unsaturated carboxylic acid and/or a derivative thereof is acrylic acid and/or a salt or ester thereof.

16. The synthetic catalyst according to claim 2, wherein the hydroxycarboxylic acid and/or a derivative thereof is lactic acid and/or a salt or ester thereof, and wherein the unsaturated carboxylic acid and/or a derivative thereof is acrylic acid and/or a salt or ester thereof.

17. The synthetic method according to claim 5, wherein the hydroxycarboxylic acid and/or a derivative thereof is lactic acid and/or a salt or ester thereof, and wherein the unsaturated carboxylic acid and/or a derivative thereof is acrylic acid and/or a salt or ester thereof.

18. The synthetic method according to claim 9, wherein the hydroxycarboxylic acid and/or a derivative thereof is lactic acid and/or a salt or ester thereof, and wherein the unsaturated carboxylic acid and/or a derivative thereof is acrylic acid and/or a salt or ester thereof.

* * * * *